United States Patent
Berry et al.

(10) Patent No.: US 10,851,340 B2
(45) Date of Patent: *Dec. 1, 2020

(54) UNITARY 3D CULTURE DEVICE

(71) Applicant: VIVABIOCELL S.p.A., Udine (IT)

(72) Inventors: Eric Berry, Udine (IT); Francesco Curcio, Udine (IT)

(73) Assignee: VIVABIOCELL SPA., Udine (IT)

(*) Notice: Subject to any disclaimer, the term of this patent is extended or adjusted under 35 U.S.C. 154(b) by 214 days.

This patent is subject to a terminal disclaimer.

(21) Appl. No.: 16/112,138

(22) Filed: Aug. 24, 2018

(65) Prior Publication Data

US 2018/0371406 A1 Dec. 27, 2018

Related U.S. Application Data

(63) Continuation of application No. 14/960,506, filed on Dec. 7, 2015, now Pat. No. 10,087,414, which is a
(Continued)

(30) Foreign Application Priority Data

Dec. 16, 2009 (EP) .................................... 09179465

(51) Int. Cl.
*C12N 5/00* (2006.01)
*C12M 1/12* (2006.01)
(Continued)

(52) U.S. Cl.
CPC .............. *C12N 5/0062* (2013.01); *A61K 9/00* (2013.01); *A61K 35/32* (2013.01); *A61L 27/18* (2013.01);
(Continued)

(58) Field of Classification Search
CPC .............. C12N 5/0062; C12N 2535/00; C12N 2533/30; C12N 2537/00; C12M 23/02;
(Continued)

(56) References Cited

U.S. PATENT DOCUMENTS

| 4,693,983 A | 9/1987 | Davies et al. |
| 6,194,210 B1 | 2/2001 | Leu et al. |

(Continued)

FOREIGN PATENT DOCUMENTS

| WO | 01/43660 | 6/2001 |
| WO | 2005012504 | 2/2005 |

(Continued)

OTHER PUBLICATIONS

European Search Report dated Nov. 28, 2013, which was issued for corresponding European Patent Application No. 13185874.8 (5 pages).

(Continued)

*Primary Examiner* — Michael L Hobbs
(74) *Attorney, Agent, or Firm* — Lucas & Mercanti, LLP

(57) ABSTRACT

A continuous device for culturing mammalian cells in a three-dimensional structure for the transplantation or implantation in vivo is described. The culturing device comprises (a) a scaffold formed by a matrix of interconnected growth surfaces spaced at regular intervals and (b) a fluid distribution means at the inlet and the exit of the growth areas. The device is particularly useful for culturing bone cells for dental implants or bone reconstruction.

11 Claims, 9 Drawing Sheets

Related U.S. Application Data continuation of application No. 13/515,685, filed as application No. PCT/EP2010/069768 on Dec. 15, 2010, now Pat. No. 9,220,731.

(51) Int. Cl.

| | | |
|---|---|---|
| *C12M 3/00* | (2006.01) | |
| *A61K 9/00* | (2006.01) | |
| *A61K 35/32* | (2015.01) | |
| *A61L 27/18* | (2006.01) | |
| *A61L 27/50* | (2006.01) | |
| *A61L 27/56* | (2006.01) | |
| *C12M 1/00* | (2006.01) | |
| *B33Y 10/00* | (2015.01) | |
| *B33Y 50/02* | (2015.01) | |

(52) U.S. Cl.
CPC .............. *A61L 27/50* (2013.01); *A61L 27/56* (2013.01); *C12M 21/08* (2013.01); *C12M 23/02* (2013.01); *C12M 25/14* (2013.01); *A61L 2300/64* (2013.01); *B33Y 10/00* (2014.12); *B33Y 50/02* (2014.12); *C12N 2533/30* (2013.01); *C12N 2535/00* (2013.01); *C12N 2537/00* (2013.01)

(58) Field of Classification Search
CPC ....... C12M 21/08; C12M 25/14; A61L 27/56; A61L 27/50; A61L 27/18; A61L 2300/64; A61K 35/32; A61K 9/00; B33Y 50/02; B33Y 10/00
USPC .................. 435/289.1, 295.21, 297.2, 297.4
See application file for complete search history.

(56) References Cited

U.S. PATENT DOCUMENTS

| | | | |
|---|---|---|---|
| 6,218,182 | B1 | 4/2001 | Naughton et al. |
| 6,283,997 | B1 | 9/2001 | Garg et al. |
| 9,220,731 | B2 * | 12/2015 | Berry .................. C12N 5/0062 |
| 9,220,732 | B2 | 12/2015 | Curcio |
| 10,087,414 | B2 * | 10/2018 | Berry ...................... A61L 27/56 |
| 2004/0010313 | A1 * | 1/2004 | Aston .................. A61L 31/088 |
| | | | 623/17.11 |
| 2005/0003530 | A1 | 1/2005 | Gerlach |
| 2005/0276791 | A1 | 12/2005 | Hansford et al. |
| 2006/0177924 | A1 | 8/2006 | Rezania et al. |
| 2009/0041825 | A1 | 2/2009 | Kotov et al. |
| 2009/0186412 | A1 | 7/2009 | Yamanaka et al. |
| 2009/0317447 | A1 * | 12/2009 | Hsiao ....................... A61F 2/28 |
| | | | 424/426 |

FOREIGN PATENT DOCUMENTS

| | | | |
|---|---|---|---|
| WO | 2005056747 | 6/2005 | |
| WO | WO-2005056747 A2 * | 6/2005 | ........... C12M 41/18 |
| WO | 2006033935 | 3/2006 | |
| WO | 2006053291 | 5/2006 | |

OTHER PUBLICATIONS

PCT International Search Report and Written Opinion dated Sep. 30, 2011, which was issued for corresponding PCT Application No. PCT/EP2010/069768 (7 pages).

PCT International Preliminary Report on Patentability completed Mar. 29, 2012, which was issued for corresponding PCT Application No. PCT/EP2010/069768 (5 pages).

European Extended Search Report dated Jul. 2, 2018, which was issued by European Patent Office for corresponding European Patent Application No. 18169764.0 (5 pages).

\* cited by examiner

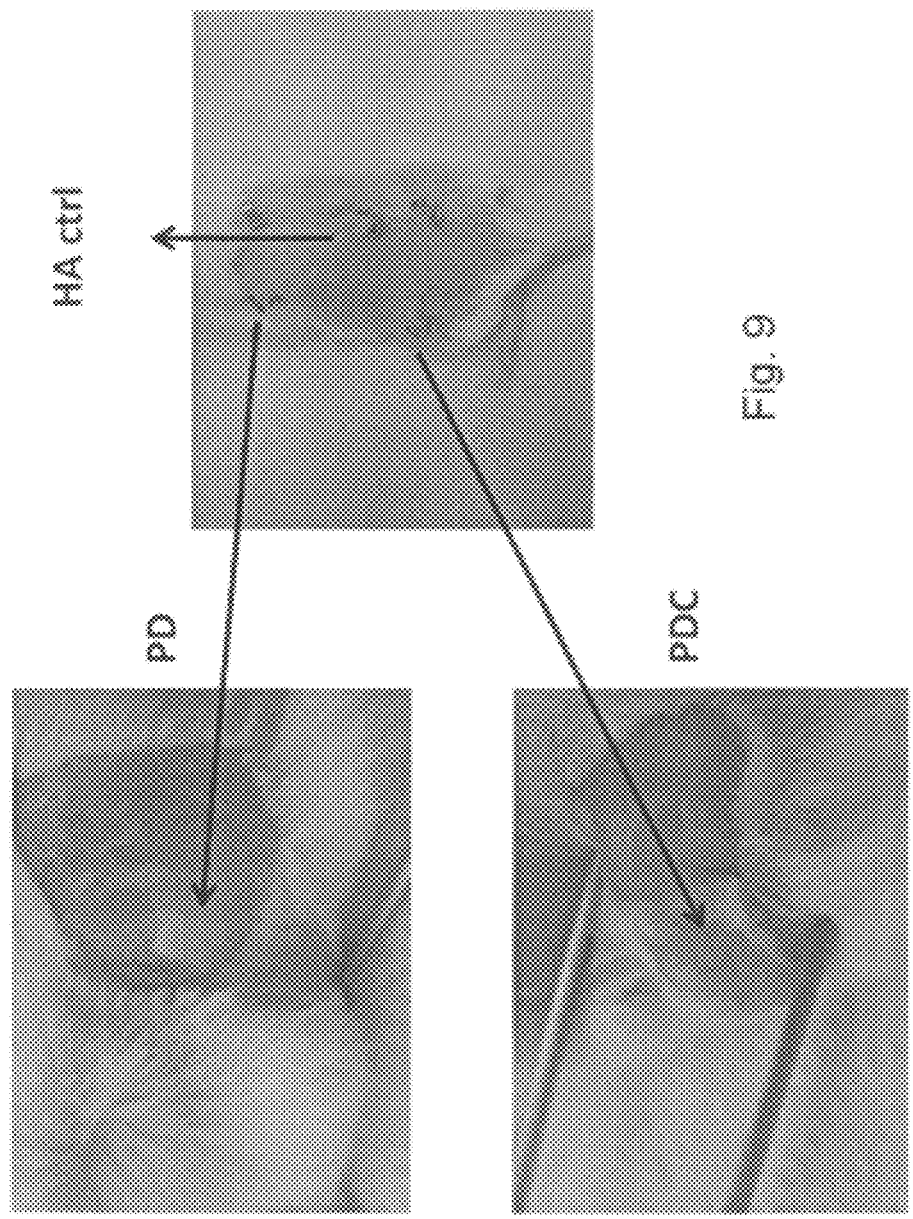

UNITARY 3D CULTURE DEVICE

CROSS-REFERENCE TO RELATED APPLICATION

This application is a Continuation of U.S. patent application Ser. No. 14/960,506 filed Dec. 7, 2015, now U.S. Pat. No. 10,087,414, which is a Continuation of U.S. patent application Ser. No. 13/515,685 filed Oct. 23, 2012, now U.S. Pat. No. 9,220,731, which is a 371 of PCT Patent Application No. PCT/EP2010/069768 filed Dec. 15, 2010, which in turn claims the benefit of European Patent Application No. 09179465.1 filed Dec. 16, 2009, the contents of each of which are incorporated herein by reference in their entirety.

FIELD OF THE INVENTION

The present invention relates to a device for culturing mammalian cells in a three-dimensional structure for the transplantation or implantation in vivo. More particularly, the present invention relates to a continuous culturing device for culturing bone cells for dental implants or bone reconstruction.

BACKGROUND OF THE INVENTION

There is increasing interest in growing cells in three-dimensional (3D) environments such as on a 3D structure or scaffold. Cell culture on 3D scaffolds is useful in tissue engineering for the generation of implantable tissue structures. Intrinsic difficulties with 3D cultures in 3D scaffolds are (i) the uniform and efficient seeding of cells throughout the scaffold pores, and (ii) limited mass transfer to the cells in the central scaffold part.

The past three decades have shown great advances in the area of tissue engineering but the problem associated with the difficulty of culturing cells at the center of deep or thick structures remains.

U.S. Pat. No. 6,194,210 describes a process for hepatitis A virus in an aggregated microcarrier-cell culture.

U.S. Pat. No. 6,218,182 describes a method for culturing 3D tissues, in particular liver tissue for use as an extracorporeal liver assist device, in a bioreactor where cells are seeded and provided with two media flows, each contacting a different side of the cells.

US 2009/0186412 describes a porous cell scaffold and methods for its production.

All prior art references address the problems that arise when a culture system with a high density of cells encounters flow irregularities.

Known bioreactors do not efficiently simulate in vivo nutrient mechanism in thick structures or when culture density is high.

Regulation of flow, delivery of nutrients, gasses and removal of waste in the bodies of mammals is an automated process that encompasses many complex functions in the body.

Blood is a complex system, that supports the ability to transport large quantities of gasses and nutrients to and from cells throughout the body. Flow is managed by a complex system that automatically alters volume and pressure to redistribute the flow of blood to areas of high demand. The distribution system includes thousands of branches and each branch may have smaller internal diameters until finally arriving at the dimensional level where the cells are nourished.

SUMMARY OF THE INVENTION

The use of Computational Fluid Dynamics (CFD) software permits analysis of the flow within a complex structure and its container. When a suitable combination of characteristics are identified, the metabolic parameters can be studied to assure that both the utilisation rate of materials and the production of waste products remain in a typically safe zone. One example would be to calculate the maximum cell density and the oxygen consumption rate, to assure that all the cells remain aerobic.

We have now found a continuous culture device which solves the problem of culturing cells at the center of deep or thick structures.

Object of the present invention is a continuous culture device comprising (a) a scaffold formed by a matrix of interconnected growth surfaces spaced at regular intervals and (b) a fluid distribution means at the inlet and the exit of the growth areas.

The spacing and definition are arranged to permit directional flow through and around the growth surfaces uniformly.

The fluid distribution means at the inlet and the exit of the growth areas permits an adequate flow to each growth surfaces. The fluid distribution is analysed using computational fluid dynamics and key metabolite utilisation analysis to assure that the cells are not subject to detrimental growth conditions.

Preferably, the fluid distribution means distributes the incoming flow of fresh nutrients and gasses to the growth surfaces. The cross-sectional area of the distribution device channels and the number of channels can be adjusted to facilitate the uniform distribution to the growth surfaces, depending on the shape of the growth surfaces and the total number of cells supported by the growth surfaces.

Preferably, the culture device includes a matrix of interconnected growth surfaces, defined by the interconnection of multiple fibers or three-dimensional structures, in an organized and repetitive manner, which can incorporate any number of facets or surface artefacts utilised to encourage or enhance the attachment and growth of cells.

The three-dimensional structures forming the matrix can be cylindrical, rectangular, hexagonal or any other shape or combination of shapes and the surfaces may be smooth or textured.

In a practical preferred embodiment of the invention, the scaffold is formed by a matrix of interconnected growth surfaces spaced at regular intervals around a central support.

The open spaces formed by the interconnection of the structures, are equal or larger than 0.7 mm and smaller than 3 mm, preferably equal or larger than 0.9 mm and smaller than 3 mm. The spacing in the preferred embodiment is greater than 1.0 mm, but can be altered as required by the need for physical strength of the scaffold. In a still more preferred embodiment of the present invention, the interconnected growth surfaces are spaced at regular intervals equal or larger than 1.0 mm and less than 2.0 mm.

Spacing is a characterizing feature of the present invention. The variability of the parameter around the above range allows to optimize the flow of medium throughout the scaffold and, at the same time, to impart an adequate solidity to the 3D structure for all the devices according to the invention independently from their final shape and dimension.

The open spaces formed by the interconnection of the growth surfaces create the organised characterizing structure of the device of the present invention which differs from the porous structure of the device known from the prior art.

The shape of the scaffold is preferably cubic but it could be another shape, for example cylindrical or anatomically correct.

Preferably, the culture device includes a large number of interconnected growth surfaces uniformly arranged to create large open areas that limit the maximum number of cells per cubic volume facilitating the easy vascularization of the growth areas.

The culture device can be made of any biocompatible material.

Biocompatible materials are any biocompatible organic polymer or mixture thereof as well as blends or mixtures of biocompatible organic polymers with biocompatible organic or inorganic non-polymeric compounds.

Non limitative specific examples of components of the biocompatible material useful in the present invention are polycaprolacton, polyethylene oxide—terephthalate, polyamide, poly-L-lactic acid, polyglycolic acid, collagen, fibronectin, hydroxyapatite, etc.

In a practical preferred embodiment, the culture device further comprises an aseptically sealed housing that can be disassembled at the completion of the culture period. Said aseptic housing can include a sealed removable cover, an inlet distribution means, an optional exit distribution means, and the necessary support means required to locate and secure the growth surfaces in the culture device.

The housing can be in the form of a rectangle, cylinder or any other shape necessary to hold the culture device and provide additional features for aseptic removal of the scaffold. The present invention offers several advantages over previous culture devices in that nutrient delivery permits the creation of and maintaining the viability of tissue on a thick (>1 mm) substrate.

The 3D culture device of the present invention can be produced in a single step process.

Alternatively, a 2D layer can be produced first, and then the single 2D layers can be assembled one over the others to form the 3D culture device according to the present invention.

The final dimension of the 3D culture device will depend on the number of assembled 2D layers.

The culture device of the present invention can be efficiently used for culturing any kind of cells into a 3D tissue. Preferably it is used for culturing cells for dental implants or bone reconstruction. Once the cells have grown into a 3D tissue, the media flow may be stopped and the tissue can be used or preserved for future use.

The culture device of the present invention can be efficiently used also for culturing cells directly into the body. In fact, the device can be implanted into the patient in need of tissue reconstruction and the culturing is effected in vivo.

By using the culture device according to the present invention cells may be grown in a controlled environment on a biodegradable scaffold. The large open areas formed by the interconnection of the growth surfaces allows them to be exposed to a uniform flow of medium and to prevent fouling during the growth process. In particular, fouling or blockade of the growth surface by gas bubbles during the growth process is prevented.

Moreover, with the culture device of the invention, culture conditions are monitored continuously and any departures from the desired conditions are automatically corrected and alarmed. This provides conditions necessary to maintain cells in their undifferentiated state, to minimise the maximum cell density and the associated toxic necrosis, and to provide an environment that is not diffusion limited for key nutrients and gasses. Furthermore the culture device according to the present invention provides the growth of tissues also in the absence of cells, as shown in experiments carried out on rabbits.

EXAMPLE

Experimental Protocol

A two-layer scaffold (11 mm×11 mm×5 mm) according to the present invention, cut in four pieces of equal dimension, was used for the cell growth experiment on mice.

Histological Analysis and Results

The four continuous culturing devices were implantated into immunodeficient NOD/SCID mice.

The analysis of the inflammatory reaction after one week from the implantation showed no sign of typical inflammatory reaction, i.e. swelling, redness, exudates, etc.

Histological analysis of the control material HA (Hydroxy Apatite), i.e. a biomedical material commercially available used as standard sample, did not reveal phlogosis (e.g. lymphocytic infiltration) conversely it revealed the integration of the porous ceramic material with the tissues (fibroblast colonization of the material's pores).

Poly-capro-lactone was removed from all the samples containing the continuous culturing device object of the present invention and was replaced by paraffin. It resulted in a negative or empty image on microphotographs.

Histological analysis of the samples P (Polycaprolactone), PC (Polycaprolactone with cells), PD (Polycaprolactone with tri-calcium phosphate dipping) (FIG. 7), and PDC (Polycaprolactone with tri-calcium phosphate dipping with cells) (FIG. 8) did not reveal any tissue's inflammatory process. Then the implantation in vivo of the continuous culturing device object of the present invention, provided cell growth without involving tissue's inflammation process.

The analysis carried out on mice demonstrated that the continuous culturing device is biocompatible and not locally toxic. Moreover the characteristic 3D structure of the continuous culturing device provides the tissue's regrowth.

The present invention is now illustrated in more details in the following drawings which represent specific embodiments of the invention without limiting it.

DETAILED DESCRIPTION OF THE DRAWINGS

Figure 1:
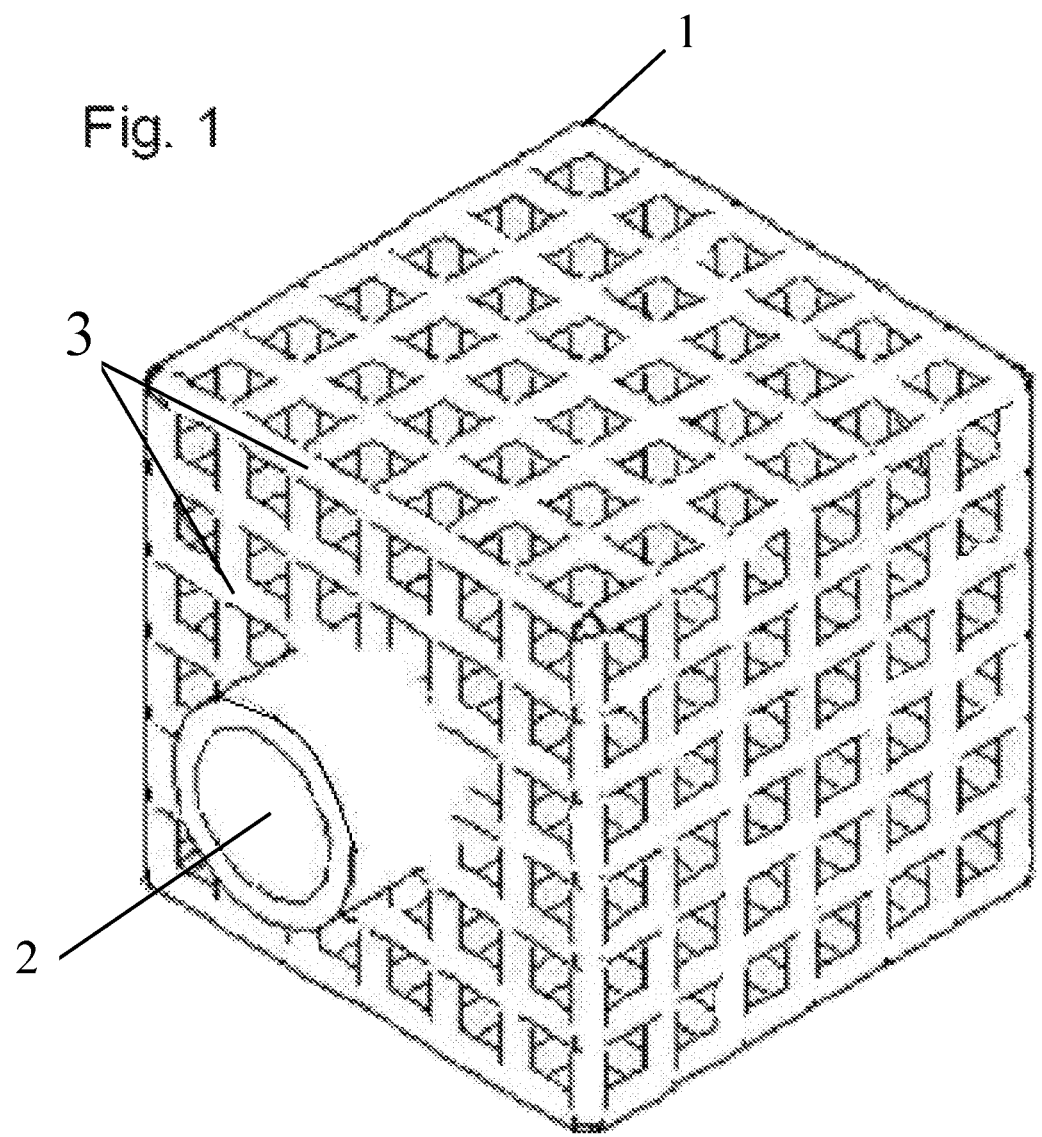
FIG. 1 One embodiment of the scaffold
FIG. 2 One embodiment of a flow distribution device
FIG. 3 One embodiment of scaffold between two flow distribution devices
FIG. 4 System flow chart
FIG. 5 CFD Flow analysis
FIG. 6 Photographic Flow analysis
FIG. 7 Microphotograph of the sample PD
FIG. 8 Microphotograph of the sample PDC
FIG. 9 Photographs of samples HA, PD and PDC

FIG. 1 is one embodiment of the scaffold. Scaffold (1) is formed by the interconnection of a matrix of cylindrical (3) structures. The scaffold (1) is formed around the central support (2).

Figure 2:
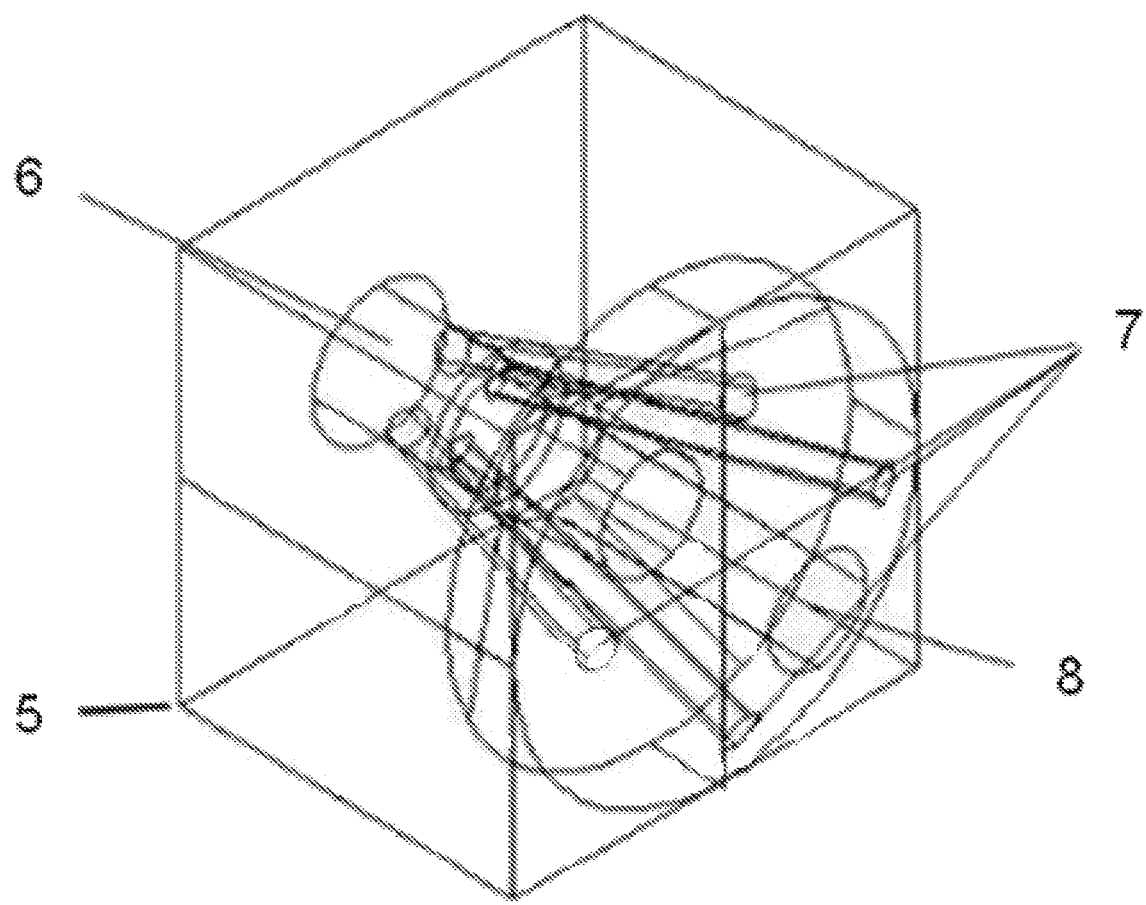

FIG. 2 is one embodiment of the fluid distribution device (5). In this device, the fluid is presented to the device (5) at a common conduit (6) which is connected to the distribution conduits (7). A support means (8) is shown to connect with the central support (2) of the scaffold (1).

Figure 3:
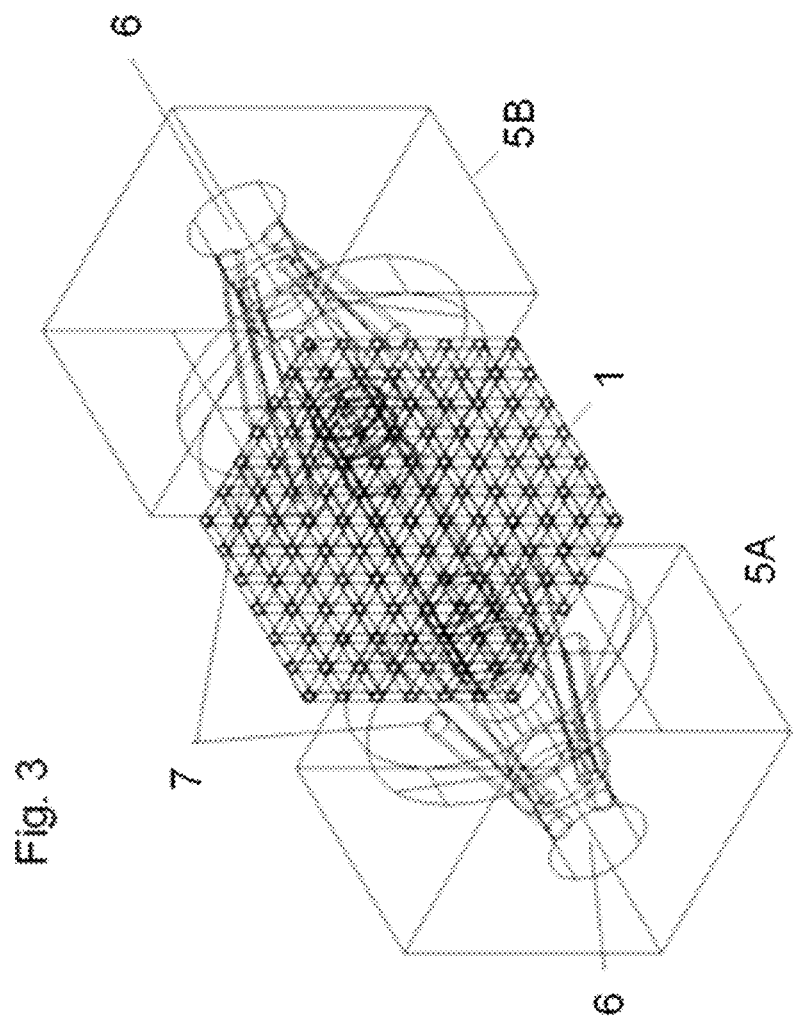

FIG. 3 depicts a scaffold (1) positioned between two of the distribution devices (5). In this embodiment the fluid is delivered to the inlet common conduit (6) and further distribute to distribution conduits (7) and then is distributed through and around the open structures (4) of scaffold (1). The fluid is then collected and presented to common conduits (7), located in the outlet device (5B) where it is collected and presented to the common conduit (6) of the distribution device (5B).

Figure 4:
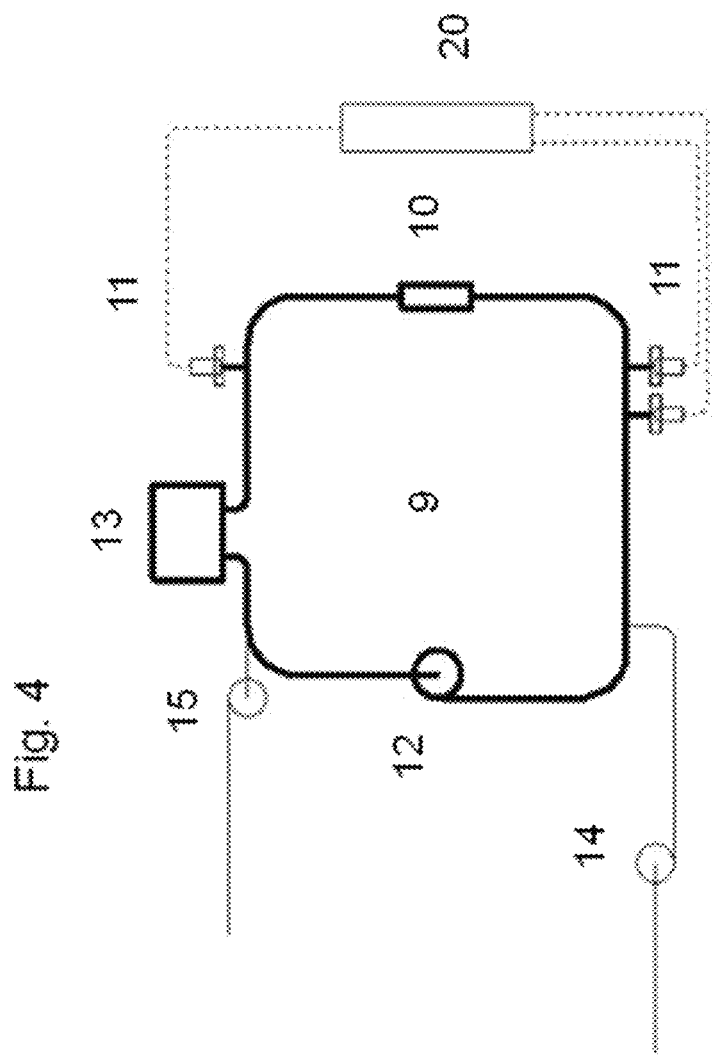

FIG. 4 is an outline view of the culture device (10) connected to a central circulation system (9). When the culture device (10) is connected to system (9), it is positioned to receive a continuous flow of nutrients and dissolved gasses provided by pump (12). A central circulation loop is created by connecting the outlet of pump (12) with the inlet of the culture device (10). The outlet of the culture device (10) is connected with the inlet of pump (12) through the fluid reservoir (13). In constant communication with the fluid in the system (12) are a variety of sensors (11). The sensors (11) are connected with a control means (20) that monitors and controls the conditions of system (12). Additional pumps (14, 15) are provided to supply metered delivery of fresh nutrients to the system, and waste materials from the system.

Figure 5:
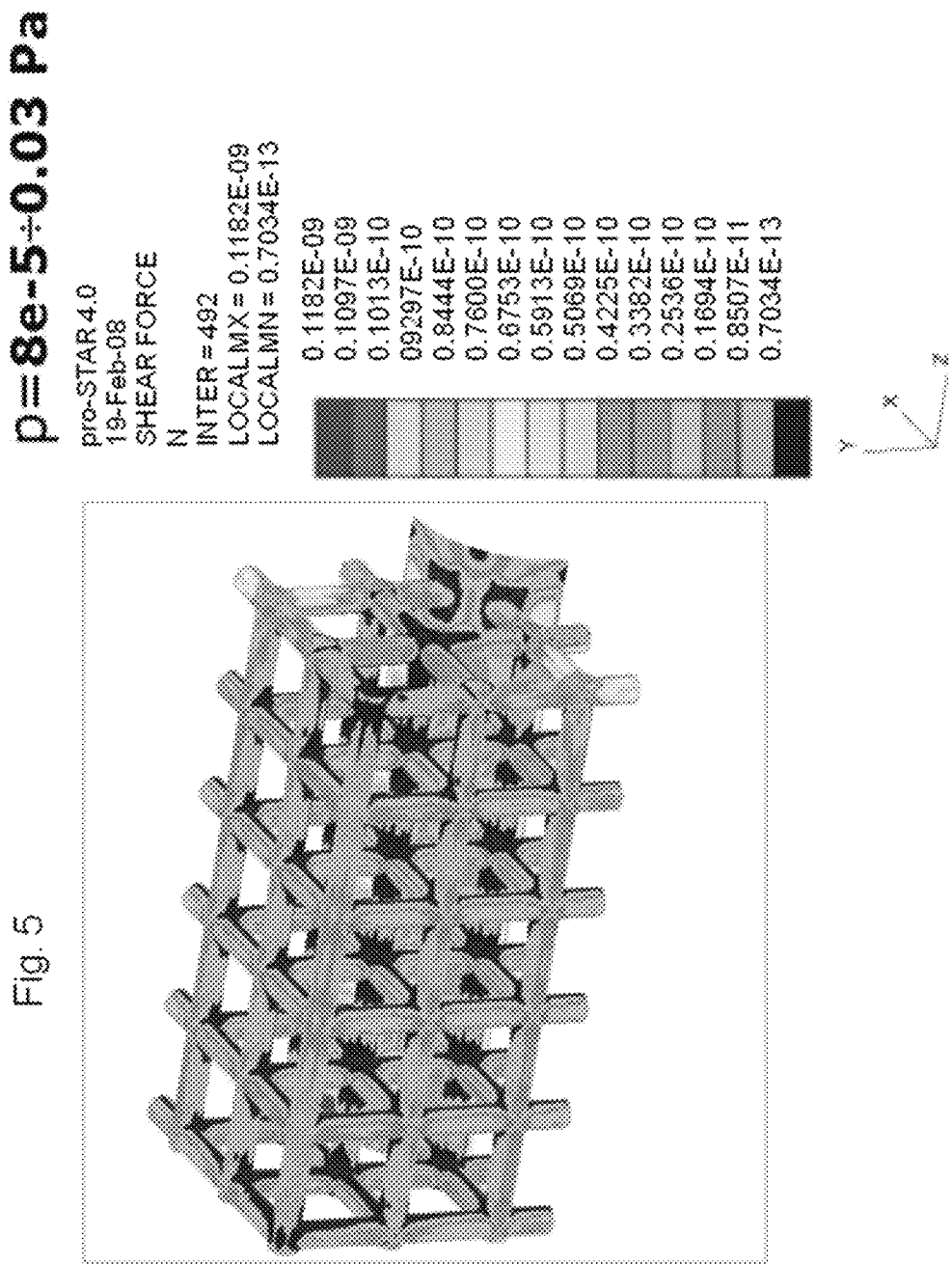

FIG. 5 illustrates an example of Computational Fluid Dynamics analysis, where the distribution of flow is throughout the structure.

Figure 6:
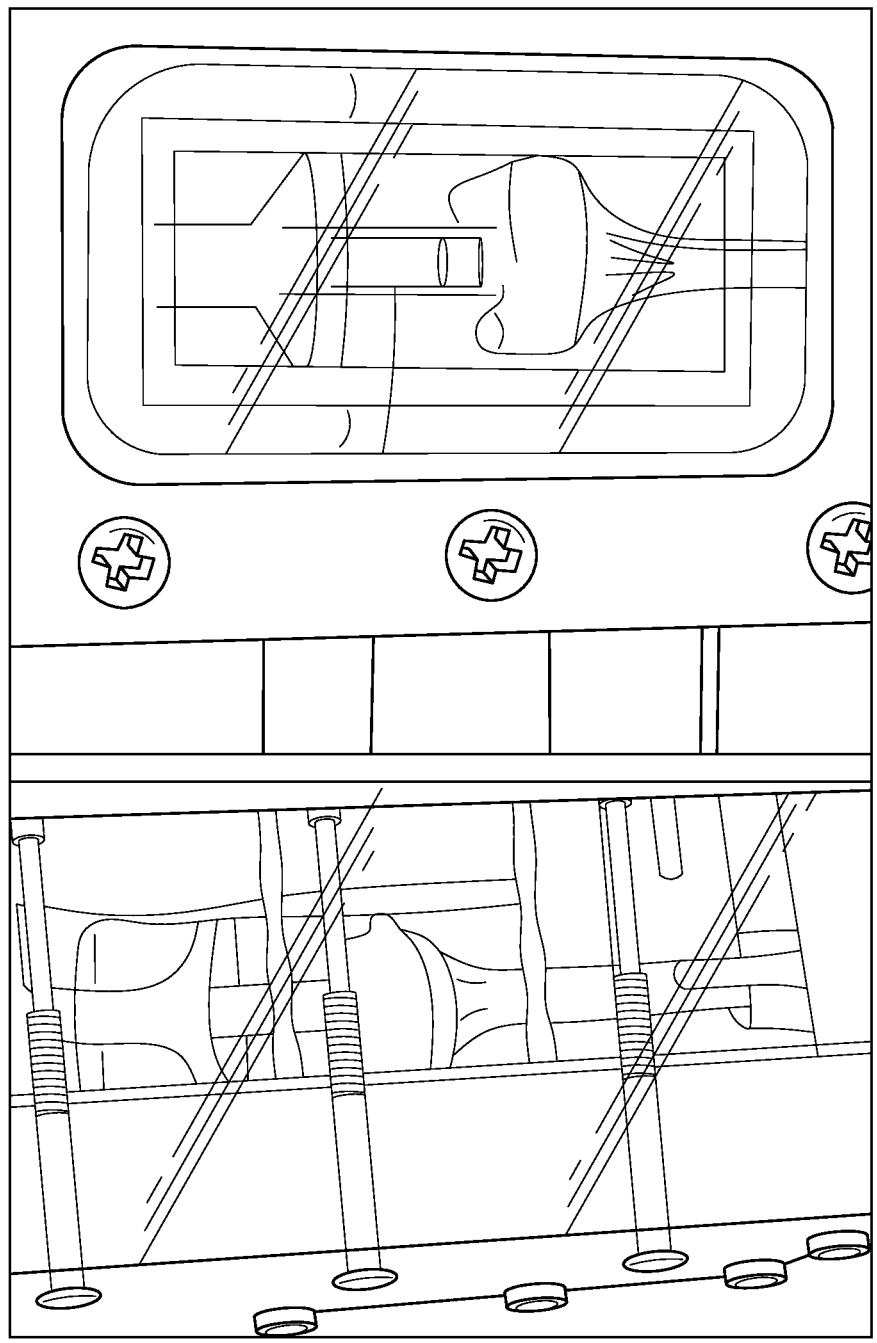

FIG. 6 is a photographic flow analysis.

Figure 7:
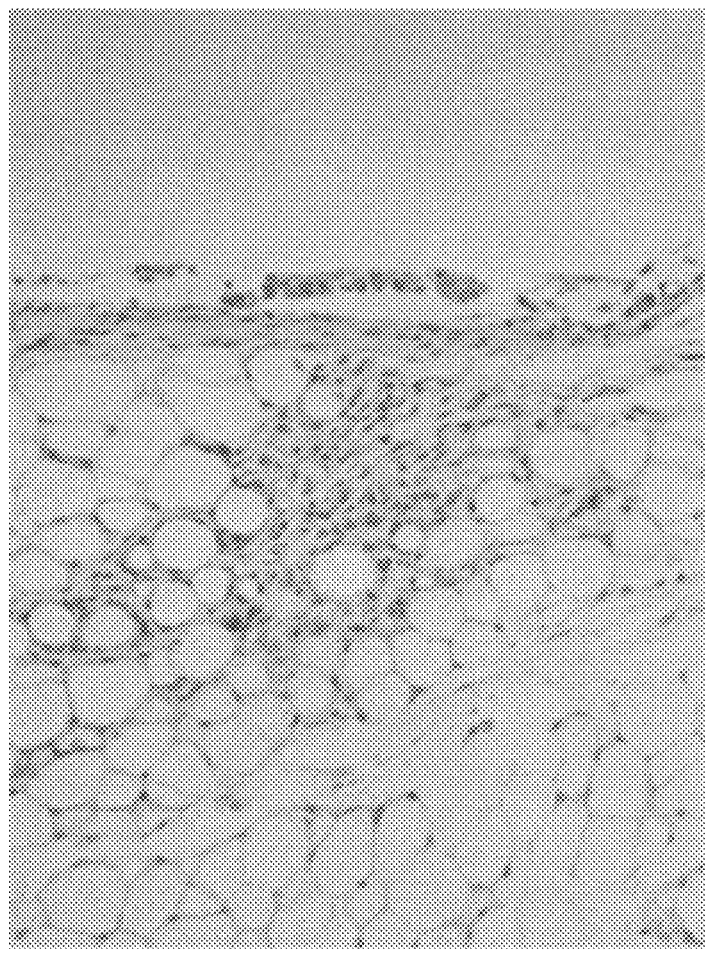
Figure 8:
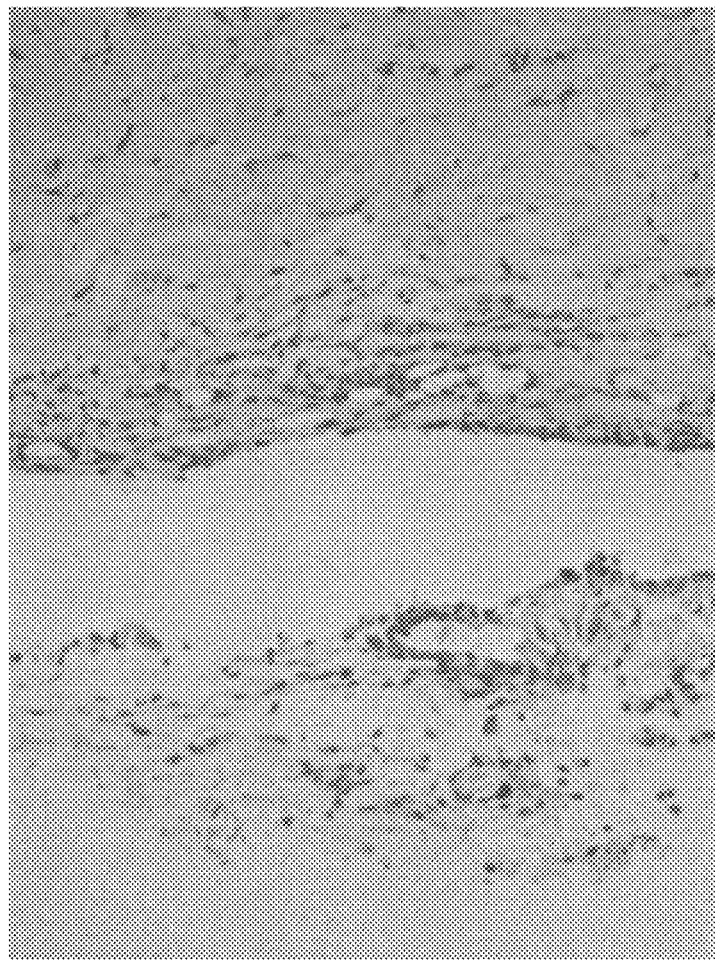

FIG. 7 and FIG. 8 illustrate the growth of cells and the absence of inflammatory process for the sample PD and the sample PDC respectively. Microphotographs are 20× of magnification and the cutis are on the top of the microphotographs.

FIG. 9 illustrates the areas of application and analysis of the samples HA, PD and PDC for the cells growth experiments on mice. The external analysis of the samples does not reveal any fibrotic reaction or inflammation process.

The invention claimed is:

1. A 3D lattice-shaped scaffold for tissue growth, the scaffold comprising:
   a 3D matrix of interconnected growth surfaces all uniformly spaced at regular and repetitive intervals, the interconnected growth surfaces provided by a first set of elongated three-dimensional structures extending in a first direction, a second set of elongated three-dimensional structures extending in a second direction different from the first direction, and a third set of set of elongated three-dimensional structures extending in a third direction different from the first direction and second direction; and
   a plurality of interconnected open spaces defined by the interconnected growth surfaces, the plurality of interconnected open spaces all being uniformly spaced at regular and repetitive intervals thereby allowing fluid to flow through the plurality of interconnected open spaces;
   wherein the uniform spacing of the interconnected open spaces provide an optimized fluid flow distribution through the scaffold; and
   wherein the elongated three-dimensional structures comprise fibers.

2. The 3D scaffold according to claim 1, wherein the interconnected fibers have one of the following shapes: cylindrical shape, rectangular shape, and hexagonal shape.

3. The 3D scaffold according to claim 1, wherein the three-dimensional structures comprise solid cylindrical structures.

4. The 3D scaffold according to claim 1, wherein the interconnected growth surfaces are textured.

5. The 3D scaffold according to claim 1, wherein the interconnected growth surfaces are spaced at regular intervals from 0.7 mm to 3 mm.

6. The 3D scaffold according to claim 5, wherein the interconnected growth surfaces are spaced from 0.9 mm to 2 mm.

7. The 3D scaffold of claim 1, wherein the interconnected growth surfaces are of a biocompatible material.

8. The 3D scaffold according to claim 7, wherein the scaffold comprises 2D layers of the biocompatible material assembled onto each other thereby providing the interconnected growth surfaces.

9. The 3D scaffold according to claim 5, wherein the biocompatible material includes at least one of the following: polycaprolacton, polyethylene oxide—terephthalate, polyamide, poly-L-lactic acid, polyglycolic acid, collagen, fibronectin, and hydroxyapatite.

10. The 3D scaffold according to claim 1, wherein the elongated three-dimensional structures of each set are parallel to each other.

11. The scaffold according to claim 1, wherein the first set of structures, the second set of structures and the third set of structure intersect with each other thereby providing each side of the scaffold with at least one edge of continuous material.

\* \* \* \* \*